(12) United States Patent
Andreev et al.

(10) Patent No.: US 10,520,426 B2
(45) Date of Patent: *Dec. 31, 2019

(54) PEAKFORCE PHOTOTHERMAL-BASED DETECTION OF IR NANOABSORPTION

(71) Applicant: Bruker Nano, Inc., Santa Barbara, CA (US)

(72) Inventors: Gregory O. Andreev, Goleta, CA (US); Chanmin Su, Ventura, CA (US)

(73) Assignee: Bruker Nano, Inc., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/666,477

(22) Filed: Aug. 1, 2017

(65) Prior Publication Data

US 2018/0106715 A1 Apr. 19, 2018

Related U.S. Application Data

(63) Continuation of application No. 15/256,071, filed on Sep. 2, 2016, now Pat. No. 9,719,916, which is a continuation of application No. 14/962,971, filed on Dec. 8, 2015, now abandoned, which is a continuation of application No. 14/618,863, filed on Feb. 10, 2015, now Pat. No. 9,207,167, which is a continuation of application No. 14/217,099, filed on Mar. 17, 2014, (Continued)

(51) Int. Cl.
*G01N 21/17* (2006.01)
*G01Q 30/02* (2010.01)
*G01Q 60/32* (2010.01)
*G01Q 30/20* (2010.01)
*B82Y 35/00* (2011.01)
*G01N 21/3563* (2014.01)

(52) U.S. Cl.
CPC ............ *G01N 21/171* (2013.01); *B82Y 35/00* (2013.01); *G01N 21/3563* (2013.01); *G01Q 30/02* (2013.01); *G01Q 30/20* (2013.01); *G01Q 60/32* (2013.01); *G01N 2201/06113* (2013.01); *G01N 2201/10* (2013.01); *G01N 2201/12* (2013.01)

(58) Field of Classification Search
None
See application file for complete search history.

(56) References Cited

U.S. PATENT DOCUMENTS 5,254,854 A * 10/1993 Betzig .................... B82Y 20/00
250/234
8,402,819 B2 * 3/2013 Dazzi ..................... B82Y 35/00
73/105

(Continued)

FOREIGN PATENT DOCUMENTS

WO WO-2010065131 A2 * 6/2010 ............. B82Y 35/00
WO WO-2010065131 A3 * 7/2010 ............. B82Y 35/00

*Primary Examiner* — Andrew Smyth
(74) *Attorney, Agent, or Firm* — Boyle Fredrickson S.C.

(57) ABSTRACT

An apparatus and method of performing photothermal chemical nanoidentification of a sample includes positioning a tip of a probe at a region of interest of the sample, with the tip-sample separation being less than about 10 nm. Then, IR electromagnetic energy having a selected frequency, ω, is directed towards the tip. Using PFT mode AFM operation, absorption of the energy at the region of interest is identified. Calorimetry may also be performed with the photothermal PFT system.

12 Claims, 5 Drawing Sheets

Related U.S. Application Data now Pat. No. 8,955,161, which is a continuation-in-part of application No. 13/306,867, filed on Nov. 29, 2011, now Pat. No. 8,650,660, which is a continuation-in-part of application No. 12/618,641, filed on Nov. 13, 2009, now Pat. No. 8,739,309.

(60) Provisional application No. 61/802,094, filed on Mar. 15, 2013, provisional application No. 61/417,837, filed on Nov. 29, 2010, provisional application No. 61/114,399, filed on Nov. 13, 2008.

(56) References Cited

U.S. PATENT DOCUMENTS

| | | | |
|---|---|---|---|
| 8,646,109 B2 * | 2/2014 | Hu | G01Q 10/065 73/105 |
| 8,650,660 B2 * | 2/2014 | Shi | G01Q 10/065 850/5 |
| 8,955,161 B2 * | 2/2015 | Andreev | B82Y 35/00 850/1 |
| 9,046,492 B1 * | 6/2015 | Prater | G01N 21/658 |
| 9,207,167 B2 * | 12/2015 | Andreev | B82Y 35/00 |
| 2006/0260388 A1 * | 11/2006 | Su | G01Q 60/34 73/105 |

* cited by examiner

PEAKFORCE PHOTOTHERMAL-BASED DETECTION OF IR NANOABSORPTION

CROSS-REFERENCE TO RELATED APPLICATIONS

The present application is a continuation of U.S. Pat. No. 9,719,916, issued Aug. 1, 2017 (U.S. application Ser. No. 15/256,071, filed Sep. 2, 2016), which is a continuation of U.S. application Ser. No. 14/962,971, filed Dec. 8, 2015, which is a continuation of U.S. Pat. No. 9,207,167, issued Dec. 8, 2015 (U.S. application Ser. No. 14/618,863, filed Feb. 10, 2015), which is a continuation of U.S. Pat. No. 8,955,161, issued Feb. 10, 2015 (U.S. application Ser. No. 14/217,099, filed Mar. 17, 2014), which claims priority from provisional application U.S. App. No. 61/802,094, filed on Mar. 15, 2013, each of which is entitled Peak Force Photothermal-based Detection of IR Nanoabsorption. U.S. Pat. No. 8,955,161 is also a continuation-in-part of U.S. application Ser. No. 13/306,867 (U.S. Pat. No. 8,650,660), filed Nov. 29, 2011, which is a non-provisional of U.S. App. No. 61/417,837, filed Nov. 29, 2010, both entitled Method and Apparatus of Using Peak Force Tapping Mode to Measure Physical Properties of a Sample, which in turn is a continuation-in-part of U.S. application Ser. No. 12/618,641 (U.S. Pat. No. 8,739,309), filed Nov. 13, 2009, which is a non-provisional of U.S. App. No. 61/114,399, filed Nov. 13, 2008, both entitled Method and Apparatus of Operating a Scanning Probe Microscope.) The subject matter of these applications is hereby incorporated by reference in their entirety.

BACKGROUND OF THE INVENTION

Field of the Invention

The preferred embodiments are directed to making nano-identification sample property measurements, and more particularly, using Peak Force Tapping® mode AFM and IR electromagnetic excitation for localized photothermal nanoID imaging and spectroscopy.

Description of Related Art

The interaction between a sample under test and radiated energy can be monitored to yield information concerning the sample. In spectroscopy, dispersion of light from a sample into its component energies can be measured and, for example, intensity plotted as a function of wavelength. By performing this dissection and analysis of the dispersed light, users can determine the physical properties of the sample, such as temperature, mass, and composition.

Notably, making spectroscopic measurements with a spatial resolution on the nanoscale is continuing to improve. However, despite ongoing progress in the development of imaging techniques with spatial resolution beyond the diffraction limit, simultaneous spectroscopic implementations delivering chemical specificity and sensitivity on the molecular level have remained challenging. Far-field localization techniques can achieve spatial resolution down to about 20 nm by point-spread function reconstruction but typically rely on fluorescence from discrete molecular or quantum dot emitters, with limited chemically specific information.

One technology for improving spectroscopic measurement performance is scanning probe microscopy. Scanning probe microscopes (SPMs), such as the atomic force microscope (AFM), are devices which typically employ a probe having a tip and causing the tip to interact with the surface of a sample with appropriate forces to characterize the surface down to atomic dimensions. Generally, the probe is introduced to a surface of a sample to detect changes in the characteristics of a sample. By providing relative scanning movement between the tip and the sample, surface characteristic data can be acquired over a particular region of the sample and a corresponding map of the sample can be generated.

A typical AFM system is shown schematically in FIG. 1. An AFM 10 employing a probe device 12 including a probe 14 having a cantilever 15. Scanner 24 generates relative motion between the probe 14 and sample 22 while the probe-sample interaction is measured. In this way images or other measurements of the sample can be obtained. Scanner 24 is typically comprised of one or more actuators that usually generate motion in three orthogonal directions (XYZ). Often, scanner 24 is a single integrated unit that includes one or more actuators to move either the sample or the probe in all three axes, for example, a piezoelectric tube actuator. Alternatively, the scanner may be an assembly of multiple separate actuators. Some AFMs separate the scanner into multiple components, for example an XY scanner that moves the sample and a separate Z-actuator that moves the probe. The instrument is thus capable of creating relative motion between the probe and the sample while measuring the topography or some other surface property of the sample as described, e.g., in Hansma et al. U.S. Pat. No. RE 34,489; Elings et al. U.S. Pat. No. 5,266,801; and Elings et al. U.S. Pat. No. 5,412,980.

In a common configuration, probe 14 is often coupled to an oscillating actuator or drive 16 that is used to drive probe 14 at or near a resonant frequency of cantilever 15. Alternative arrangements measure the deflection, torsion, or other motion of cantilever 15. Probe 14 is often a microfabricated cantilever with an integrated tip 17.

Commonly, an electronic signal is applied from an AC signal source 18 under control of an SPM controller 20 to cause actuator 16 (or alternatively scanner 24) to drive the probe 14 to oscillate. The probe-sample interaction is typically controlled via feedback by controller 20. Notably, the actuator 16 may be coupled to the scanner 24 and probe 14 but may be formed integrally with the cantilever 15 of probe 14 as part of a self-actuated cantilever/probe.

Often a selected probe 14 is oscillated and brought into contact with sample 22 as sample characteristics are monitored by detecting changes in one or more characteristics of the oscillation of probe 14, as described above. In this regard, a deflection detection apparatus 25 is typically employed to direct a beam towards the backside of probe 14, the beam then being reflected towards a detector 26. As the beam translates across detector 26, appropriate signals are transmitted to controller 20, which processes the signals to determine changes in the oscillation of probe 14. In general, controller 20 generates control signals to maintain a relative constant interaction between the tip and sample (or deflection of the lever 15), typically to maintain a setpoint characteristic of the oscillation of probe 14. For example, controller 20 is often used to maintain the oscillation amplitude at a setpoint value, As, to insure a generally constant force between the tip and sample. Alternatively, a setpoint phase or frequency may be used.

A workstation 40 is also provided, in the controller 20 and/or in a separate controller or system of connected or stand-alone controllers, that receives the collected data from the controller and manipulates the data obtained during scanning to perform point selection, curve fitting, and distance determining operations.

AFMs may be designed to operate in a variety of modes, including contact mode and oscillating mode. Operation is accomplished by moving either the sample or the probe assembly up and down relatively perpendicular to the surface of the sample in response to a deflection of the cantilever of the probe assembly as it is scanned across the surface. Scanning typically occurs in an "x-y" plane that is at least generally parallel to the surface of the sample, and the vertical movement occurs in the "z" direction that is perpendicular to the x-y plane. Note that many samples have roughness, curvature and tilt that deviate from a flat plane, hence the use of the term "generally parallel." In this way, the data associated with this vertical motion can be stored and then used to construct an image of the sample surface corresponding to the sample characteristic being measured, e.g., surface topography. In one mode of AFM operation, known as TappingMode™ AFM (TappingMode™ is a trademark of the present assignee), the tip is oscillated at or near a resonant frequency of the associated cantilever of the probe. A feedback loop attempts to keep the amplitude of this oscillation constant to minimize the "tracking force," i.e. the force resulting from tip/sample interaction. Alternative feedback arrangements keep the phase or oscillation frequency constant. As in contact mode, these feedback signals are then collected, stored, and used as data to characterize the sample. Note that "SPM" and the acronyms for the specific types of SPMs, may be used herein to refer to either the microscope apparatus or the associated technique, e.g., "atomic force microscopy." In a recent improvement on the ubiquitous TappingMode™, called Peak Force Tapping® (PFT) Mode, feedback is based on force as measured in each oscillation cycle.

Regardless of their mode of operation, AFMs can obtain resolution down to the atomic level on a wide variety of insulating or conductive surfaces in air, liquid, or vacuum by using piezoelectric scanners, optical lever deflection detectors, and very small cantilevers fabricated using photolithographic techniques. Because of their resolution and versatility, AFMs are important measurement devices in many diverse fields ranging from semiconductor manufacturing to biological research.

Infrared (IR) spectroscopy is a useful tool in many analytical fields such as polymer science and biology. Conventional IR spectroscopy and microscopy, however, have resolution on the scale of many microns, limited by optical diffraction. It has become apparent that it would be particularly useful to perform IR spectroscopy on a highly localized scale, on the order of biological organelles or smaller, at various points on a sample surface. That way, information about the composition of the sample, such as location of different materials or molecular structures, would be possible.

Conventional infrared (IR) spectroscopy is a widely used technique to measure the characteristics of material. In many cases, the unique signatures of IR spectra can be used to identify unknown material. IR spectroscopy is performed on bulk samples which gives compositional information but not structural information. Infrared spectroscopy allows collection of IR spectra with resolution on the scale of many microns. Near-field scanning optical microscopy (NSOM) has been applied to some degree in infrared spectroscopy and imaging. While there have been some advancement with NSOM, the field is still in need of a sensitive and reliable commercial instrument. At this time, no widely available instrument provides routine IR spectra with resolution below the diffraction limit. One technique based on use of an AFM to produce such localized spectra is described in a publication entitled "Local Infrared Microspectroscopy with Sub-wavelength Spatial Resolution with an Atomic Force Microscope Tip Used as a Photo-thermal Sensor" (PTIR) Optics Letters, Vo. 30, No. 18, Sep. 5, 2005. The technique is also discussed in US Pub. No. 2009/0249521 (The '521 publication), the entirety of which is expressly incorporated by reference herein. Those skilled in the art will comprehend the details of the technique in the publication but the technique will be described briefly herein for clarity.

Referring to the '521 publication, in PTIR, infrared radiation is incident on a region of a sample. At a wavelength absorbed by the sample, the absorption will typically cause a local increase in temperature and a rapid thermal expansion of the sample. A probe is arranged to interact with the sample and transducer to generate a signal related to the IR energy in the region under the probe tip. "Interact" means positioning the probe tip close enough to the sample such that a probe response can be detected in response to absorption of IR radiation. For example, the interaction can be contact mode, tapping mode or non-contact mode. An associated detector can be used to read one or more probe responses to the absorbed radiation. The induced probe response may be a probe deflection, a resonant oscillation of the probe, and/or a thermal response of the probe (e.g., temperature change). For probe deflection and/or resonant oscillation of the probe, appropriate detectors can include split segment photodiodes along with any associated amplification and signal conditioning electronics. In the case of a thermal response, the appropriate detector may comprise, for example, a Wheatstone bridge, a current and/or voltage amplifier and/or other associated electronics to sense, amplify, and condition the thermal signal from the probe. The probe response is then measured as a function of the wavelength of incident radiation to create an absorption spectrum. From the spectra, material in the sample can be characterized and/or identified.

As noted in the '521 publication, an AFM set-up used for the published work on IR spectroscopy is shown. The sample is mounted on a ZnSe prism, or prism made from other suitable materials, which does not absorb the radiation of interest. A pulsed IR source, in this case a Free Electron Laser beam, is directed into the prism. The prism is made at an angle such that the beam is in Total Internal Reflection in order for the beam to be propagative in the sample and evanescent in the air. Thus, only the sample is significantly exposed to the laser radiation, and the AFM probe is minimally exposed to the beam. The Free Electron Laser (FEL) is an IR source that is both variable in wavelength and has a pulsed output. Free Electron Lasers are large expensive facilities. The probe is placed at a point on the sample by the scanner and is held at an average height by feedback electronics. Both the vertical and lateral deflection signal, as well as the feedback signal, may be monitored.

When the FEL is pulsed, the sample may absorb some of the energy, resulting in a fast thermal expansion of the sample as shown in FIG. 3. This has the effect of a quick shock to the cantilever arm, which, if the ability of the cantilever to respond to this shock is slower than the shock, will result in exciting a resonant oscillation in the cantilever arm. Because the absorbed energy is ideally contained within the sample, this shock is due primarily to rapid sample expansion, as minimal IR energy is absorbed by the cantilever itself. Although the probe is kept in contact with the surface by the feedback electronics, the resonant signal is too fast for the feedback electronics, but can be observed directly from the photodetector. Thus the cantilever rings down while still in contact with the surface, an effect called "contact resonance". The absolute deflection, amplitude, and frequency characteristics of the contact resonance vary with the amount of absorption, as well as other properties, such as the local hardness, of the localized area around the probe tip, for example, by analyzing the ringdown and/or the Fourier transform (FFT) of the ringdown events. Also, depending on the direction of the expansion, vertical resonances, lateral resonances, or both can be excited. By repeating the above process at varying wavelengths of the FEL, an absorption spectra on a localized scale is achieved. By scanning the probe to various points on the sample surface and repeating the spectra measurement, a map of IR spectral surface characteristics can be made. Alternatively, the wavelength of the FEL can be fixed at a wavelength that is characteristic of absorption of one of the components of the sample. The probe can then be scanned across the sample surface and a map of the location of that component can be generated.

Although the set-up as described is promising, there is no real possibility of commercializing the same. First, the IR light source used, the Free Electron Laser, is a very large and expensive facility, as noted. Moreover, alternative benchtop sources of IR radiation have been limited by one or more characteristics that have made them unsuitable for a widely available instrument.

As further noted in the '521 publication, the apparatus described in the literature suffers from other limitations beyond the expensive and stationary IR source. The apparatus employs a bottoms-up illumination scheme that requires a sample to be placed on a specially fabricated IR transmitting prism. In addition to being costly and easy to damage, this arrangement requires special sample preparation techniques to prepare a sample thin enough such that the IR light can penetrate the sample to reach the probe. Further, the actual signals generated can be small, thus requiring averaging of the signal and limiting the bandwidth of the technique. More sensitivity is required to address a wider range of potential samples.

The applicant associated with the '521 publication contends that the system disclosed therein can be used to obtain IR spectra from highly localized regions of a sample, allowing discrimination and/or identification of the composition of a micro or nano-sized region of a sample. The system may be used for mapping the variations in IR absorption over a wider area of a sample, by imaging the energy absorbed at one or more wavelengths. One additional problem, however, is leakage of heat from a region that actually is absorbing the excitation energy, to a region that is not. When using PTIR, as the sample is heated (i.e., a region of interest exhibits absorbing characteristics), the heat may, and often does, leak toward surrounding regions of the sample. If the probe scans a location that is indirectly heated, the instrument may identify that location as being responsive to the IR excitation and conclude it is absorbing, when in fact it was not. Clearly, this can lead to compromised data and/or poor resolution. Independent of its ability to provide localized spectroscopy, an improved IR microscopy instrument that can provide efficient localized spectroscopic measurements was desired.

Despite ongoing progress in the development of imaging techniques with spatial resolution beyond the diffraction limit, spectroscopic implementations delivering chemical specificity and sensitivity on the molecular level have remained challenging. Again, far-field localization techniques can achieve spatial resolution down to about 20 nm by point-spread function reconstruction but typically rely on fluorescence from discrete molecular or quantum dot emitters, with limited chemically specific information. Scanning near-field optical microscopy (SNOM) provides sub-diffraction-limited resolution through the use of tapered fibers or hollow waveguide tips. However, aperture-limited and wavelength-dependent fiber throughput reduces sensitivity, generally making SNOM unsuitable for spectroscopic techniques that have low intrinsic signal levels.

In scattering-type SNOM (s-SNOM) external illumination of a sharp (metallic or semi-conducting) probe tip can enhance sensitivity, spectral range, and spatial resolution. Chemical specificity can be obtained through the implementation of, for example, IR vibrational s-SNOM, tip-enhanced coherent anti-Stokes Raman spectroscopy (CARS), or tip-enhanced Raman scattering (TERS). Here the antenna or plasmon resonances of the (noble) metal tips can provide the necessary field enhancement for even single-molecule sensitivity.

In the standard implementation, however, the direct illumination of the tip apex results in a three-to-four orders of magnitude loss in excitation efficiency, related to the mode mismatch between the diffraction-limited far-field excitation focus and the desired tens of nanometers near-field localization, as determined by the tip apex radius. The resulting loss of sensitivity, together with a far-field background signal, often limit contrast and may cause imaging artifacts, presenting challenges for the general implementation of a wider range of spectroscopic techniques in s-SNOM.

Given the interest in spectroscopy-related characteristics of samples on a much smaller scale, an improved instrument was desired to expand the range and efficiency of performing optical imaging and spectroscopy for chemical identification on the nanoscale.

SUMMARY OF THE INVENTION

Using Peak Force Tapping® mode AFM, the preferred embodiments overcome the drawbacks with the prior art, including PTIR, by directing light overhead of the sample and locally exciting the photothermal response at the tip-sample interface. Resolution is improved and sample preparation is minimized.

In one preferred embodiment, a method of locally measuring IR absorption of a sample, the method includes causing a probe to interact with a sample in an oscillating mode of AFM operation, and then directing a locally amplified IR signal at a sample. The method identifies a change in modulus based on the directing step to provide an indicator of IR absorption by the sample. Measuring techniques sensitive to modulus change, such as peak force tapping (PFT) AFM mode, or contact resonance mode, may be employed.

In another preferred embodiment, a method of photothermal chemical nanoidentification of a sample includes positioning a tip of a probe at a region of interest of the sample, the tip-sample separation being less than about 10 nm. Then IR electromagnetic energy having a selected frequency, $\omega$, is directed towards the tip. Using PFT mode AFM operation, absorption of the energy at the region of interest is identified.

In another aspect of the preferred embodiments, the method further includes obtaining a spectrum of the sample by tuning the selected frequency to a range of frequencies.

According to a further aspect of the preferred embodiments, a method of photo thermal nanocalorimetry on a sample using an AFM operating in Peak Force Tapping® mode includes positioning a tip at a region of interest of the sample. The method then directs IR electromagnetic energy having a selected frequency, ω, towards the tip, and determines a mass of the region by obtaining 3D topography data corresponding to the region in response to the directing step. A ΔT in response to the directing step is also determined to ultimately provide an indication of heat capacity.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENTS

An improved apparatus and method of performing chemical identification of a sample includes combining monochromatic IR excitation at a selected frequency with Peak Force Tapping® (PFT) AFM configured for making mechanical property measurements. Purely mechanical detection of IR nanoabsorption by a sample is realized, thereby facilitating chemical nanoidentification of a region of the sample.

Nanoscale Chemical Identification

Figure 1:
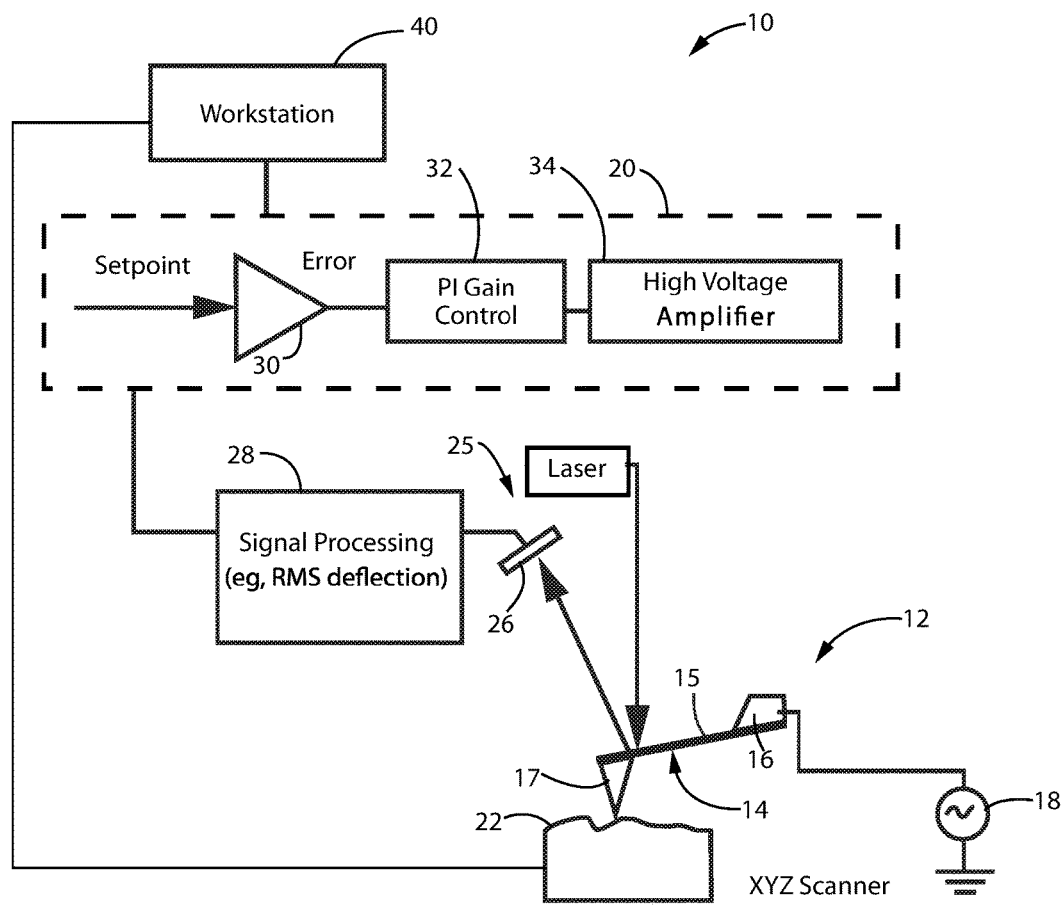
FIG. 1 is a schematic illustration of a Prior Art atomic force microscope AFM.
Figure 2:
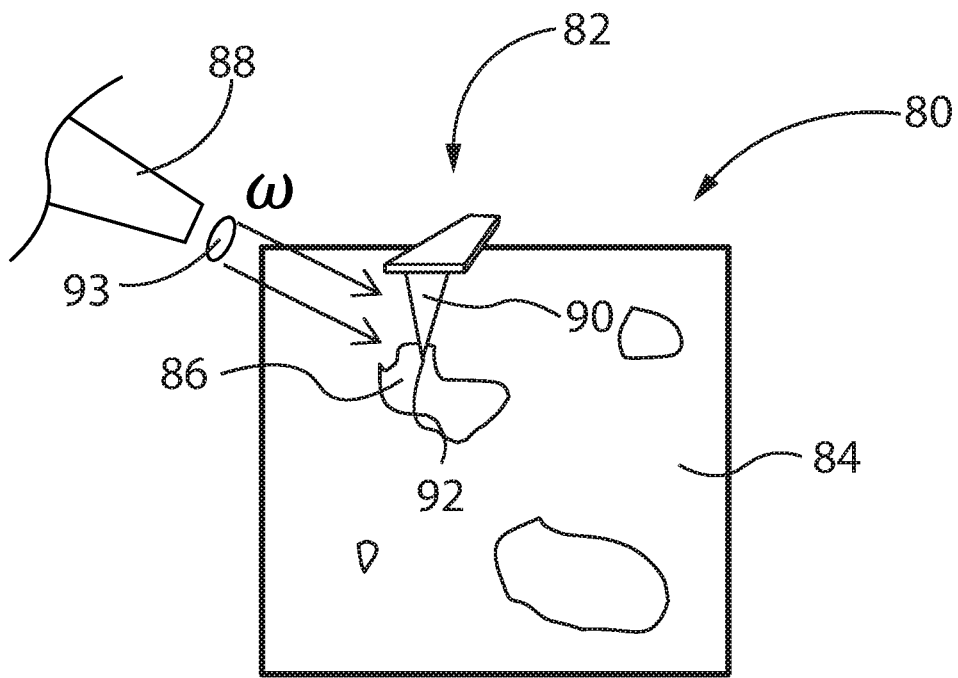
FIG. 2 is a schematic illustration of a PeakForceIR experimental set-up according to a preferred embodiment, including an AFM probe tip excited by an IR source and interacting with a sample.

Turning initially to FIG. 2, a PeakForceIR apparatus 80 includes a PFT probe 82 that is introduced to a sample 84, and in particular, a region of interest 86. A source of IR electromagnetic radiation 88 directs light toward a tip 90 of probe 82, tip 90 including an apex of nanoscale dimensions 92 that primarily interacts with the surface of sample 84.

Figure 3:
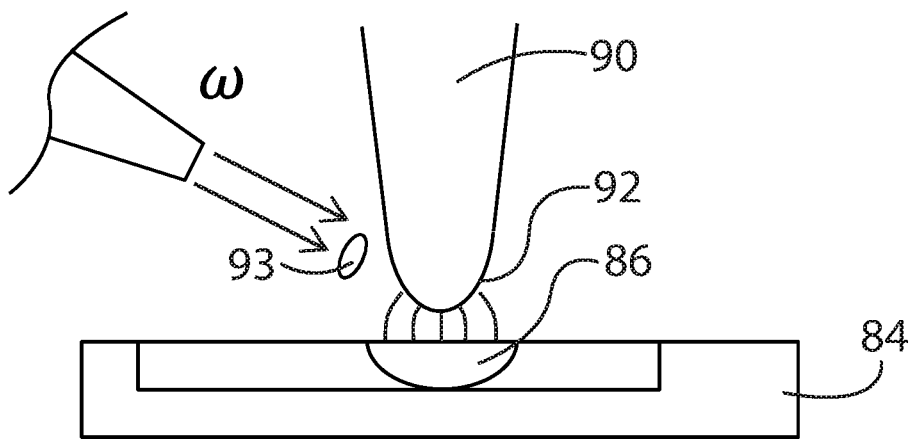
FIG. 3 is a schematic front view of a PFT probe of the PeakForceIR apparatus, illustrating localized heating of a sample region of interest.

FIG. 3 illustrates more specifically the localized heating of the sample provided by the IR source. Source 88 directs IR light at a selected frequency, ω, toward sample 84 with an optical element (e.g. a lens) 93 focusing the light on tip 92 which through the lightning rod effect or an optical resonance (e.g. plasmonic) creates an enhanced, localized electric field 94 in the nanoscale gap between tip apex 92 and the sample 84 surface region of interest. If the material directly underneath the tip apex 92 is able to absorb the monochromatic IR light at the IR frequency, i.e. it has a nonzero imaginary index of refraction at said frequency: Imag(n(w))>0, such as in the case of a molecular resonance, then a temperature rise will occur due to the absorption of energy from the IR light by the sample region. Essentially, a nanoscale "hot spot" under the tip is created. This temperature rise may cause a measurable change in a mechanical property, i.e. elastic modulus, of the sample region, detectable by mechanical property measurement techniques such as PFT mode AFM.

By tuning the IR frequency (for example, sweeping), the user can obtain a spectrum of a sample region's change in mechanical properties as a function of IR frequency. The largest mechanical property change will occur for the largest temperature change, which in turn takes place at IR frequencies corresponding at or near the absorption maximum of the sample, specifically at the maximum of Imag($r_p$(k,w)), where $r_p$(w) is the in-plane momentum (k) dependent, p-polarized reflection coefficient of the sample surface. The in-plane momentum is largely determined by the tip radius, R, and spans a range on the order of k=0 to ~3/R. Thus a plot of the IR laser induced mechanical property change (e.g. elastic modulus Y measured with and without the IR laser illuminating the tip) vs. IR laser frequency, provides a spectrum related to Imag($r_p$(k,w)), which in turn is related to the sample region's absorption: Imag(n(w)). Locations where the largest change in mechanical properties takes place, is typically indicative of the largest temperature change and thus the largest absorption. This will provide an indication of the materials identity, since absorption lines are routinely used for chemical identification in infrared spectroscopy. If absorption does not occur at a particular (x, y) location, the light will simply be scattered and ignored in this system. Since the mechanical property measurement in the PFT AFM mode is localized to the nanoscale, the IR laser induced change in mechanical properties detected by such means would enable a nanoscale chemical identification modality.

Figure 4:
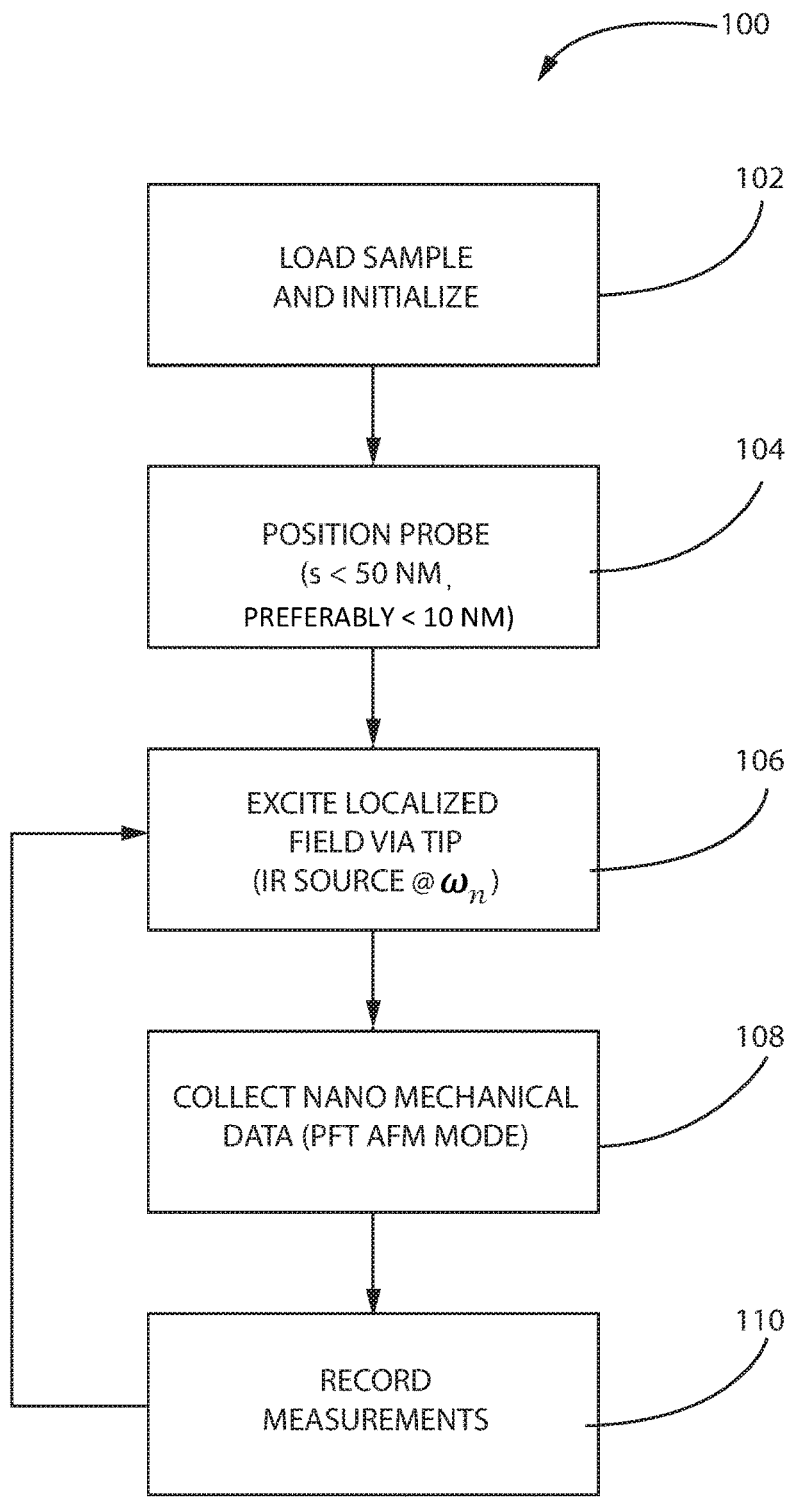
FIG. 4 is a flow diagram of a nanoidentification method using PeakForceIR, according to a preferred embodiment.
Figure 5:
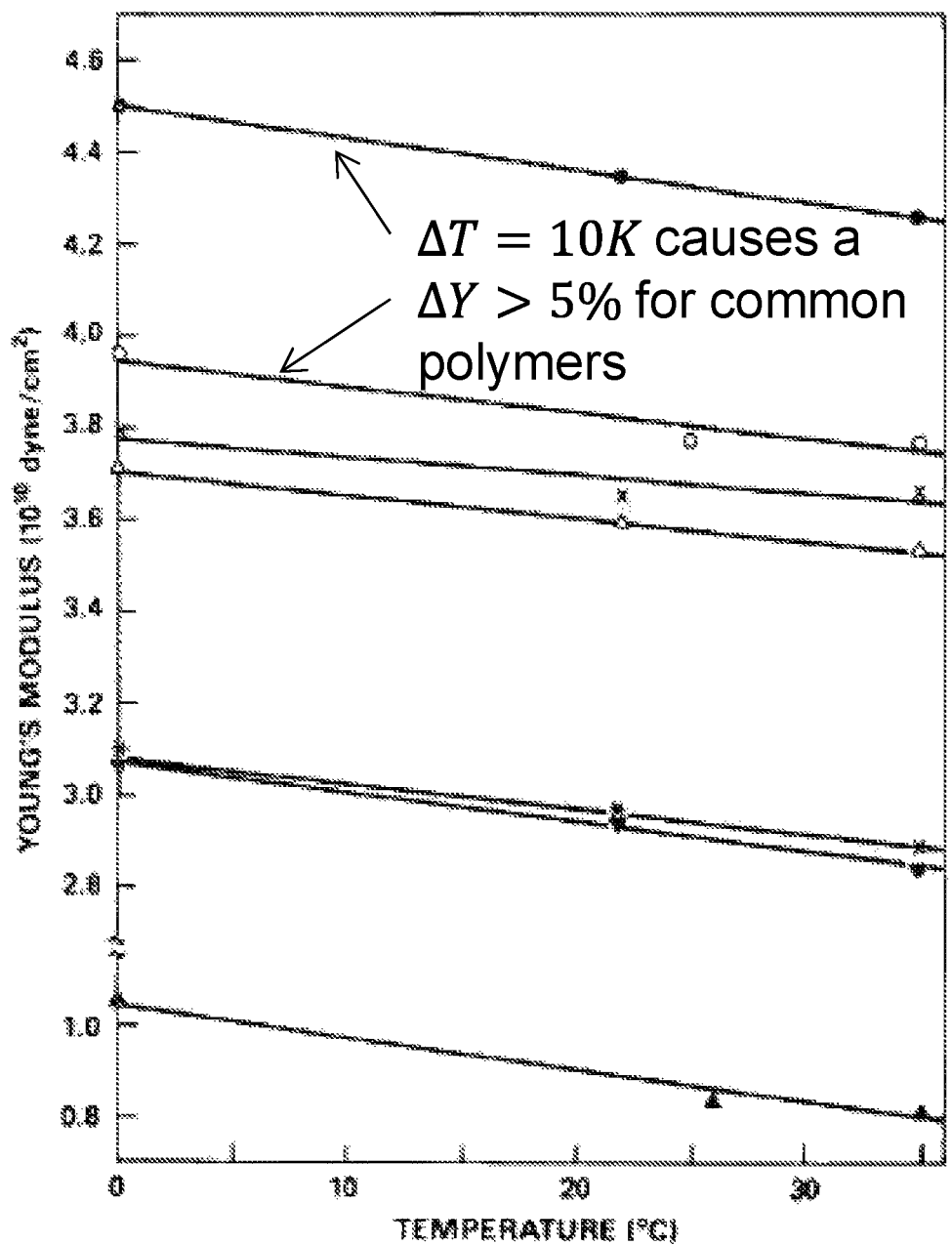
FIG. 5 is a graph of Young's modulus vs. temperature for a range of materials.

A method 100 associated with this technique is illustrated in FIG. 4. Once a sample is loaded in the instrument in Block 102, the tip-sample separation ("s") is reduced or periodically reduced to a position sufficient to create the localized enhanced electric field between the tip apex and the sample in Block 104. Then, in Block 106 the tip is illuminated by the IR monochromatic source operated at a frequency selected corresponding to an absorption line or other spectral feature for which Imag(n(w))>0 for the material in the sample the user is seeking to identify, which will create an enhanced localized field in the tip-sample gap. With the tip of the probe positioned above the region containing the material of interest, PFT mode AFM is preferably employed to detect changes in the mechanical properties, e.g., the elastic modulus of the sample, if any, in Block 108. Measurements are recorded in Block 110 and method 100 returns to Block 106 for the case in which the user would like to try to identify another material in the sample region of interest (by selecting an appropriate frequency of the IR source). As a preferred embodiment, the elastic modulus change due to the IR laser excitation is detected. An illustration of a typical plot of Young's modulus for several different materials is provided in FIG. 5. As noted, a change in temperature, ΔT of about 10 Kelvin causes a ΔY (change in Young's modulus) greater than 5% for common polymers such as polystyrene and polyvinyl chloride. As can be calculated based on the model provided in the previously mentioned PTIR publication, a temperature rise of the sample region beneath the tip on the order of 10K is achievable on a sufficiently strong IR resonance using modest power (<100 mW max power) pulsed or CW laser sources. Such a change produces a relative modulus change within the current detection sensitivity of PFT. The detection sensitivity of PFT is described in the previously identified application incorporated by reference herein namely, U.S. Ser. No. 13/306,867, filed Nov. 29, 2011, entitled Method and Apparatus of Using Peak Force Tapping Mode to Measure Physical Properties of a Sample, and demonstrated in Pittenger et al., Bruker Nano Surfaces Division Application Note #128: Quantitative Mechanical Property mapping at the Nanoscale with Peak-Force QNM (Apr. 15, 2010), which is expressly incorporated by reference herein. By using PFT, or another modulus sensitive measurement (e.g., contact resonance, in some cases, TappingMode, etc.), to record IR frequency dependent induced signals related to the Young's modulus, a spectrum of $\Delta Y(w)$ can be obtained that will be directly comparable with an FTIR absorption spectrum.

In one example, in FIG. 20B of the aforementioned '867 case, the interaction force as a function of tip-sample distance in one modulation period is shown. The elastic property of the material can be calculated conventionally by using the upper part of the slope (see segment DE in FIG. 20B, segments CDE illustrate short range repulsive interaction) using, for example, the Oliver-Pharr model, or another contact mechanical model. (see, e.g., Oliver W C and Pharr G M 2004 *Measurement of Hardness and Elastic Modulus by Instrumented Indentation: Advances in Understanding and Refinements to Methodology J. Mater. Res.* 19 Mar. 20, 2004). A benefit of the peak force tapping (PFT) control is the ability to use cantilevers from 0.01 N/m to 1000 N/m in one mode of AFM operation, thereby enabling high resolution mechanical property mapping of the broadest range of materials on a single instrument from 10 kPa to 100 GPa in elastic modulus.

In this way, direct measurement of absorption is provided (in contrast to the complex valued sSNOM near-field signal). Moreover, unlike PTIR, with the incident electromagnetic energy coming from the top of the sample (as opposed to underneath), sample selection is not limited (transparent materials, etc.), and the sample does not need to be prepared (complex slicing operation of the sample to several hundred nanometers). Overall, PeakForce IR provides an elegant solution that is easier to set-up and operate, and more cost-effective than other purely optical chemical nanoidentification methods of such as sSNOM and TERS.

Nanoscale Calorimetry with PeakForceIR

A second application using a set-up similar to that described above for PeakForceIR is nanoscale calorimetry—heat capacity. The nanoscale temperature rise of a quantifiable volume given a known input of energy, allows the user to determine nanoscale heat capacity of thermostatic materials. The heat capacity is given by, $$[C] = Q/m\Delta T \quad \text{(Equation 1)}$$

in which m is the mass, Q is the heat input and $\Delta T$ is the temperature rise. The mass is preferably provided by modeling via 3D topography, while Q is modeled from the laser power, or measured using sSNOM. The temperature rise, $\Delta T$, is preferably measured using PeakForce mode for mechanical property measurement (PeakForce QNM, the subject of the application expressly incorporated by reference herein).

Figure 6:
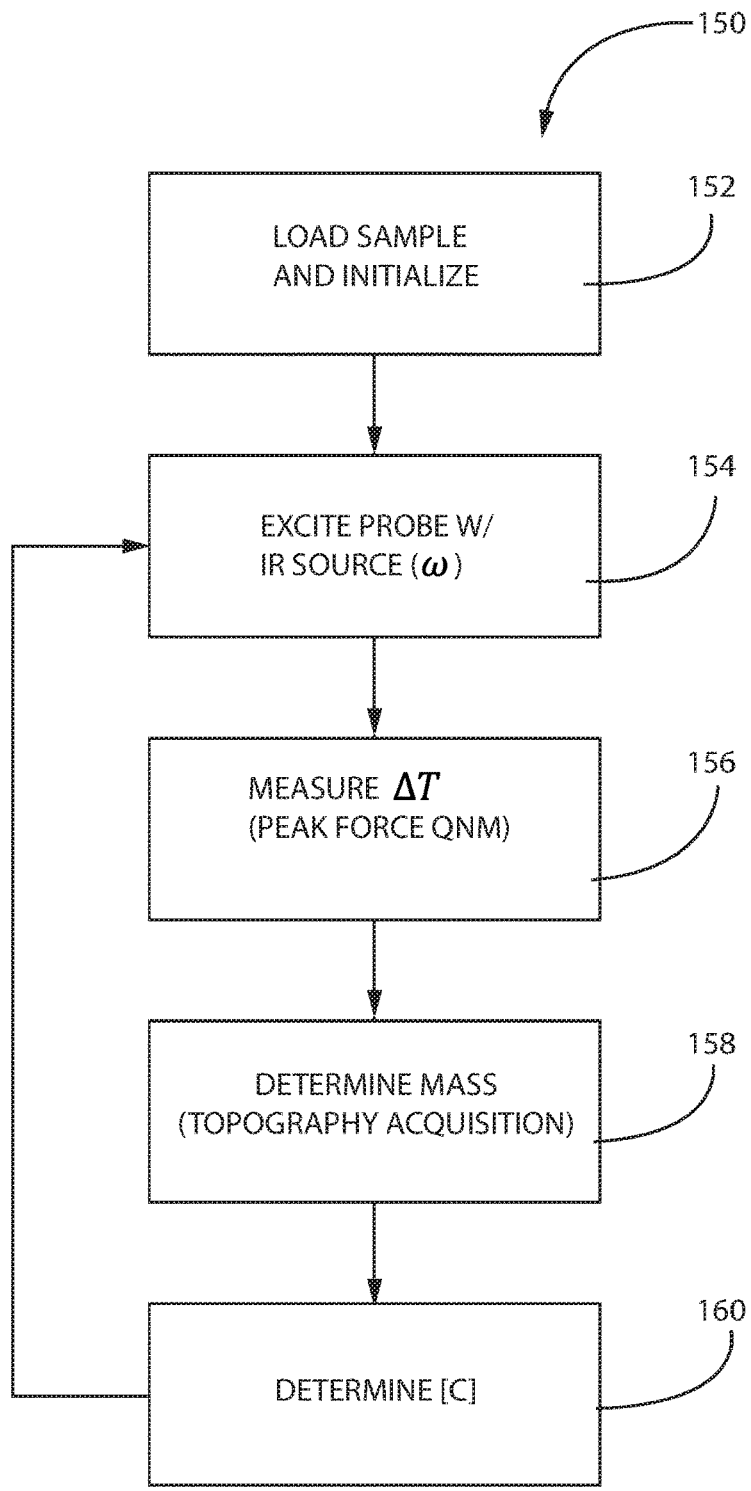
FIG. 6 is a flow diagram of a PeakForceIR method of performing nanocalorimetry, according to a preferred embodiment

A method 150 of nanoscale calorimetry is provided in FIG. 6. Upon loading a sample upon start-up and initialization in Block 152, electromagnetic energy is input to the sample via the PFT AFM tip in Block 154. The corresponding temperature rise is measured using PeakForceQNM mechanical property mapping in Block 156. Thereafter in Block 158, the mass is determined by using a 3D topography image of the region of interest. The heat capacity is then calculated (see, e.g., Eqn. 1) in Block 160 and the process is repeated for different excitation frequencies and sample locations.

IR Source

The preferred embodiments use a rapidly tunable, electronically controlled, monochromatic source of said radiation with a line width below 1 cm$^{-1}$ and a peak power of at least 1 mW, capable of operating in pulsed mode. This enables imaging at a single, well-defined frequency, while still retaining the ability to perform spectroscopy (generate a spectrum) by rapidly tuning the laser and repeating the measurement of the near field interaction. One preferred implementation of such a monochromatic source is a tunable External Cavity Quantum Cascade Laser (QCL), which is routinely capable of producing an average spectral power density of greater than 10 mW/cm$^{-1}$ with tuning ranges spanning >100 cm$^{-1}$.

As best understood, such a spectral density is at least a factor of 1000 better than other state of the art methods for producing broadband, coherent laser radiation over a bandwidth of 100 cm$^{-1}$, using methods such as difference frequency generation. The advantage in spectral power density enables the acquisition of near field signals with sufficient signal-to-noise performance for a 20×20 nm sample area on a sub-millisecond timescale. Such an acquisition rate is essential to display a near field image in real-time, simultaneously with an AFM image, for which a scan rate of 1 Hz or greater is preferred. Furthermore, when performing nanoID, oftentimes the shape of the entire spectrum is not necessary to successfully ID a sample region. The absorption at several well-chosen frequencies is oftentimes sufficient. Thus the ability to have the spectral density of a monochromatic laser at a select set of frequencies would allow for a far more rapid means of nanoidentifying a material by its chemical signature. The ability to rapidly tune the laser by as little as 0.01 cm$^{-1}$, allows a spectroscopic resolution difficult, if not impossible, to achieve with the broadband approach. Also, the user can specify an arbitrary set of frequencies of interest, which may correspond to several absorption lines, and acquire near-field signals only at those frequencies.

Secondly, the ability for the monochromatic source to operate in pulsed mode is also preferred given the following advantages, such as:

1. the ability to trigger pulses at specific times during which a near field interaction is at a desired state, i.e. a maximum or a minimum (see discussion of background subtraction/suppression below).
2. the ability to combine such laser pulses with the distance correlated signal discriminator to z-gate the near-field nanoantenna-sample surface interaction.
3. the ability to reach larger peak power during the time of the pulse (elicits a stronger near-field response—easier to detect, etc.).
4. the ability to perform a time-resolved near-field measurement.
5. less heat generation which has the potential to allow enhanced performance such as better stability and broader tenability.
6. less heat generation at the nanoantenna-sample interface, which reduces thermally induced vibrational noise in the nanoantenna structure, and also produces a less destructive measurement since the temperature of the nanoantenna and sample are increased a lesser amount than in the case of a CW excitation.
7. Typically lower cost due to a decreased design complexity and lower cooling requirements over CW (continuous wave) lasers.

Probe Design

The optimal probe for concentrating incident IR fields at the probe apex is one which can oscillate above the surface, has a tip radius below 50 nm, is an excellent optical antenna in the IR range of interest, and provides a high degree of side optical access to the probe. The quality of the probe's optical antenna effect depends on the IR conductivity of the probe's material composition, to the extent of the skin depth at the IR frequency of interest. Higher IR conductivity for the top ~10-100 nm of the probe material results in larger surface currents generated along the tip length in response to an incident IR field. Larger currents result in larger dynamic charge concentrations at the tip apex which in turn create larger localized near fields in the tip and sample gap. A smaller tip radius also serves to increase the field enhancement between the tip and sample. One embodiment of such a probe is a conventional silicon probe which has been metallized by a Platinum Iridium or Platinum Silicide coating. Such probes can also be made forward facing with a visible apex, which can enhance the side optical access to the probe. If a coated tip is used, the coating should be durable so that it does not deteriorate during scanning, causing a loss of antenna quality. Alternatively, a solid metal probe can be employed or a probe of sufficiently high carrier mobility, such as heavily doped Silicon or Diamond.

The optimal probe for nanoscale mechanical measurements of stiffness, such as those measurements performed using PeakForce QNM, requires a probe with a stiffness in an optimal range for the expected stiffness of the material being investigated. For applications involving polymers, a probe with a spring constant on the order of k>10 N/m and a tip radius R<10 nm is sufficient. For other harder or softer material classes probes with more appropriate spring constants may be optimal. The range of modulus values currently covered by available probes is approximately 700 kPa-70 GPa, as described in the aforementioned incorporated Application Note regarding PeakForce QNM.

For the combined technique described with respect to this invention, a probe that is both a highly efficient concentrator of IR light and possesses a stiffness optimized for the material category under investigation, is highly desired. Such a probe needs to be an excellent optical antenna with a high degree of optical access to the tip while being much stiffer than the typical material investigated with the IR technique described here. For instance, a Silicon probe with a forward facing tip metallized with a ~10 nm layer of Platinum Silicide or Platinum Iridium attached to a cantilever having a spring constant of 10-40 N/m is one possible choice which is already commercially available. Similarly, softer materials may be employed using a coated probe having lower spring constants, such as 0.5 N/m.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

What is claimed is:

1. A method of photo thermal nanocalorimetry on a sample using an AFM operating in Peak Force Tapping mode, the method including:
   positioning a tip at a region of interest of the sample;
   directing IR electromagnetic energy having a selected frequency, $\omega$, towards the tip;
   determining a mass of the region by obtaining 3D topography data corresponding to the region in response to the directing step; and
   determining a $\Delta T$ in response to the directing step.

2. The method of claim 1, wherein the tip has an apex with a radius between about 10 nm and 100 nm.

3. The method of claim 2, wherein the tip is made so as to concentrate IR fields along a length of the tip in response to the directing step.

4. The method of claim 3, wherein an IR conductivity of the distal 10 nm to 100 nm of the tip is higher than the remainder of the tip.

5. The method of claim 4, wherein the tip is silicon and is metalized with a Platinum Iridium or Platinum Silicide coating.

6. The method of claim 3, wherein the tip is one of a solid metal probe and a probe made of a heavily doped material.

7. The method of claim 1, further comprising calculating a heat capacity, [C], of the region according to $[C]=Q/m\Delta T$.

8. The method of claim 7, further comprising repeating each of the previous steps at a plurality of regions of interest.

9. The method of claim 7, further comprising repeating each of the previous steps at a plurality of selected frequencies, $\omega$, at the regions of interest.

10. The method of claim 1, wherein the directing step includes using an IR source that is monochromatic with a line width below 1 $cm^{-1}$ and a peak power greater than 1 mW.

11. The method of claim 10, wherein the monochromatic source is a tunable Quantum Cascade Laser (QCL).

12. The method of claim 1, wherein $\Delta T$ is measured using Peak Force QNM mode.

* * * * *